United States Patent [19]

Avetisov et al.

[11] Patent Number: 5,075,105
[45] Date of Patent: Dec. 24, 1991

[54] COMPOSITION FOR TREATMENT OF PROGRESSIVE MYOPIA

[76] Inventors: Eduard S. Avetisov, ulitsa Ramenki, II, korpus 3, kv. 629; Maya I. Vinetskaya, 16 Parkovaya ulitsa, 49, korpus I, kv. 8; Elena N. Iomdina, I Parkovaya ulitsa, I/5I, kv. 34, all of Moscow; Zulfia K. Boltaeva, ulitsa Druzhby narodov, 8a, kv. 27, Tashkent; Gennady L. Khromov, 2-aya Frunzenskaya ulitsa, 10, kv. 100, Moscow; Antonina A. Dolgopyatova, ulitsa Karla Marxa, 20, kv. 178, Moscow; Anatoly B. Davydov, ulitsa Krasny Kazanets, 19, korpus I, kv. 283, Moscow; Elena P. Tarutta, ulitsa Volgina, 19, kv. 28, Moscow; Ljudmila D. Andreeva, Nagatinskaya naberezhnaya, 34, kv. 189, Moscow, all of U.S.S.R.

[21] Appl. No.: 678,269
[22] PCT Filed: Sep. 27, 1989
[86] PCT No.: PCT/SU89/00254
 § 371 Date: Apr. 23, 1991
 § 102(e) Date: Apr. 23, 1991
[51] Int. Cl.⁵ .............................. A61K 31/79
[52] U.S. Cl. .................. 424/78.04; 424/427; 424/428; 514/499; 514/188
[58] Field of Search ............. 424/80, 81, 427, 428; 514/499

[56] References Cited

U.S. PATENT DOCUMENTS

| 4,470,965 | 9/1984 | Wolf et al. | 424/80 |
| 4,525,346 | 6/1985 | Stark | 424/80 |
| 4,615,882 | 10/1986 | Stockel | 424/80 |

Primary Examiner—Thurman K. Page
Assistant Examiner—Louis A. Piccone
Attorney, Agent, or Firm—Burgess, Ryan & Wayne

[57] ABSTRACT

The invention relates to medicine.

A composition for treatment of progressive myopia is composed of the following constituents, taken in mass percent:

| | |
|---|---|
| a mixture of polyvinylpyrrolidone, acrylamide-hydrazide, and ethylacrylate (1;1;1) | 18.8 to 29.5 |
| an aqueous solution, containing the following ingredients, taken in mg/l: | 69.5 to 80.1 |
| hydrochloric acid | 940.0 |
| boric acid | 4.12 |
| ferrous oxide | 115.0 |
| cupric citrate | 16.0 |
| 3-percent aqueous hydrogen peroxide | 0.79 to 0.89 |
| dichlorodi-[2-methyl-3-hydroxy-4,5-di-(hydroxymethyl)-pyridine] of copper (II) | 0.11 to 0.31. |

1 Claim, No Drawings

COMPOSITION FOR TREATMENT OF PROGRESSIVE MYOPIA

TECHNICAL FIELD

The present invention relates to medicine and more specifically a composition for treatment of progressive myopia.

PRIOR ART

At present a complex of therapeutic measures applied against progressive myopia involves various methods aimed at reinforcing the posterior pole of the eyeball. Alongside with conventional surgical methods search for new methods and means for operationless effects upon the sclera aimed at directional correction of the myopic process proves to be the currently central problem.

One state-of-the-art medicinal agent for treatment of progressive myopia (SU, A, 1,156,680; Ophthalmological Herald, 1985, Moscow, Meditsina Publishers, vol. 101, No. 2, pp. 31–36) is known to appear as a foaming gel-like composition, incorporating a dry mixture of polyvinylpyrrolidone, acrylamide-hydrazide, and ethylacrylate, and a dissolving mixture, consisting of ferrous chloride, cupric citrate, boric acid, hydrochloric acid, and distilled water, as well as an activator, i.e., a 3-percent hydrogen peroxide that promotes foaming of the composition. The aforesaid composition is injected under the Tenon's capsule to establish an elastic foamed gel on the scleral surface, which while being gradually replaced by the freshly formed connective tissue, adds to the strength characteristics of the sclera. However, the studies performed have demonstrated that formation of a connective capsule on the scleral surface and a process of its reinforcing occur at a relative slow rate, which is accounted for by a definite formulation of said composition, whose active components stimulate the synthesis of collagen and provide for its structural stability.

DISCLOSURE OF THE INVENTION

It is an object of the present invention to provide a composition that would be capable of accelerating the formation of a connective capsule and adding to the elastic-strength characteristics of the sclera due to qualitative and quantitative changes of starting components thereof.

Said object is accomplished due to the fact proposed herein is a composition for treatment of progressive myopia, incorporating a mixture of polyvinylpyrrolidone, acrylamide-hydrazide and ethylacrylate, an aqueous solution of an iron compound, cupric citrate, boric and hydrochloric acids, and hydrogen peroxide, said composition comprising also dichlorodi-[2-methyl-3-hydroxy-4,5-di(hydroxymethyl)pyridine] of copper (II) with the following mass-percent ratio of the starting components:

| | |
|---|---|
| mixture of polyvinylpyrrolidone, acrylamide-hydrazide and ethylacrylate (taken in equal proportions) | 18.8 to 29.5 |
| aqueous solution, containing the following ingredients, mg/l: | 69.5 to 80.1 |
| hydrochloric acid | 940.0 |
| boric acid | 4.12 |
| ferrous oxide (II) | 115.0 |
| cupric citrate | 16.0 |
| 3-percent aqueous hydrogen peroxide | 0.79 to 0.89 |
| dichlorodi-[2-methyl-3-hydroxy-4,5-di-(hydroxymethyl)-pyridine] of copper (II) | 0.11 to 0.31. |

The proposed composition promotes formation of the fresh connecting tissue, this being due intensified processes of collagen biosynthesis, as well as contributes to increases elastic-strength parameters of the scleral tissue.

PREFERRED EMBODIMENT OF THE INVENTION

The proposed composition resulting from intermixing of the mixture of polymers, the aforesaid aqueous solution, and the copper compound, should appear as a homogeneous liquid gel free from any alien inclusions, inhomogeneous components, or clumps, which is to be assessed visually.

Once having been doped with an activator (i.e., a 3-percent aqueous solution of hydrogen peroxide) the composition turns into a soft elastic foamed gel having a density (volume weight) of from 0.46 to 0.57 g/cm$^3$.

The mixture of polyvinylpyrrolidone, acrylamidehydrazide, and ethylacrylate (taken in equal proportions) that makes part of the proposed composition in an amount of 69.5 to 80.1 mass percent, proves to be a principal basic structure of the foamlike composition. The aforespecified amounts and proportions provide for a required structure of the foamed gel occurring after intermingling before use.

An aqueous solution of ferrous oxide, cupric citrate, boric and hydrochloric acids, said ingredients being taken in the aforesaid quantities and proportions, is in fact a mixture of catalyzing additives, which is used for dilution of a dry mixture of polymers and, when applied in the aforestated amounts and proportions, contributes to their polymerization and formation of a required structure of the foamed gel.

Addition of an activator to the formulation of the composition, viz. a 3-percent aqueous hydrogen peroxide, establishes a plurality of foaming centres, contributes to formation of elastic consistency of the resultant foamed hydrogel, and initiates the polymerization process that proceeds during intermixing of the ingredients. Dichlorodi[2-methyl-3-hydroxy-4,5-(hydroxymethyl)-pyridine] of copper (II), which is incorporated into the proposed composition, is engaged in formation of crosslinks in the collagen fibre, promotes formation of a connective capsule, and adds to the elastic-strength parameters of the scleral tissue.

The proposed composition has been trialled experimentally both on test animals and on patients with progressive myopia under clinical conditions. There has been studied the degree of compatibility of the copper compound with the polymer base of the composition. To this end a run of tests have been carried out, aimed at selecting an optimum concentration of said compound, as well as study into the dynamics of disengagement of said compound from the polymer composition.

The results of studies into compatibility of the copper compound with the mixture of polymers have indicated that when taken in an amount of 0.11 to 0.31 mass percent the copper compound neither disturb nor retard the process of foaming and structurization of the foamed gel.

The results of studies into the dynamics of disengagement of the copper compound from the principal polymer base have demonstrated that said compound is almost completely set free from the foamed material within eight days so that 96 percent of its initial concentration is disengaged.

Hence deposition of the copper compound in the foamed gel upon the scleral surface provides for a gradual and prolonged effect of said compound on the scleral tissue and on the processes of formation of the connective capsule.

The proposed composition has been subjected to tests for its ability to promote formation of the connective capsule and to increase the elastic-strength characteristics of the sclera, as well as for its toxic and irritative effect on the eyeball coats.

The proposed composition was prepared 'ex tempore' by mixing the copper compound, the mixture of polymers, and an aqueous solution of the aforementioned formulation. After addition of an activator, i.e. a 3-percent aqueous hydrogen peroxide, the resultant mixture was injected under the Tenon's capsule onto the posteroexternal surface of the sclera of a test rabbit.

The proposed composition was applied to a total of 42 eyes of the test rabbits belonging to the chinchilla race, whereas a foaming polymer composition of the known formulation (SU, A, 1,156,680) used in clinical practice for sclera-reinforcing injections, was introduced under the Tenon's capsule of opposite animal's eye which served as the control.

After a period of from one to six months the test animals were subjected to eyeball enucleation, and the scleral tissue was studied for biomechanical characteristics (i.e., ultimate strength, modulus of elasticity, maximum longitudinal strain). Besides, there was determined the intensity of collagen biosynthesis as an index characteristic of the process of formation of a connective capsule. There were carried out also morphological examinations of the sclera and the surrounding tissue in 12 eyes (of which six control ones) in the periods of from two weers to six months after administration of the proposed composition.

The results of the biomechanical studies performed are tabulated below.

Elastic-Strength Characteristics of the Sclera Within the Various Periods After Administration of the Proposed Composition

| Post-injection period | Experimental | | | Control | | |
|---|---|---|---|---|---|---|
| | Ultimate strength MPa | Strain, % | Modulus of elasticity, MPa | Ultimate strength MPa | Strain, % | Modulus of elasticity, MPa |
| 1 month | 8.1 | 33.0 | 25.1 | 7.6 | 36.0 | 24.5 |
| 6 months | 11.0 | 26.4 | 27.1 | 9.0 | 29.1 | 25.3 |

It is evident from the data tabulated above that the effect of the proposed composition on the scleral tissue increases its elastic-strength characteristics within shorter periods of time compared with the control. One month after the injection the ultimate strength of the sclera tissue was by 6.6 percent higher than the corresponding control data, whereas its maximum longitudinal strain was found to be lower by 9 percent.

Six months after the begining of the experiment the sclera-reinforcing effect of the proposed composition got still more pronounced, that is, the ultimate strength exceeded the control figures by 22.2 percent, while the maximum longitudinal strain was by 10.2 percent below the corresponding percentage of the sclera of the control eyes.

There was also found, within different periods of time after application of the proposed composition, the level of the collagen biosynthesis, using $^{14}C$-proline having a specific radioactivity of 125 $\mu$C/mole. It has been found that within a 1.5-month observation period the rate of collagen biosynthesis equals 267±17 pulse/min per milligram of dry tissue, while the respective figures in the control specimens is lower (245±12 pulse/min per milligram of dry tissue). Another 2.5 to 3 months later the intensity of collagen biosynthesis remains high, i.e. 287±21 pulse/min per milligram of dry tissue against 260±23 pulse/min per milligram of dry tissue in the control. A higher level of collagen synthesis is indicative of a higher rate of the process of formation of a connective capsule under the effect of the proposed composition. Thus, the thickness of the capsule in three months after the injection equals 146 $\mu$m on the average, whereas the thickness of the capsule in the same period after injection of the known polymer composition (SU, A, 1,156,680) is as low as 109 $\mu$m.

Morphological examinations of a local reaction of the organism to the injection of the proposed composition failed to reveal any injurious, toxic or irritative effect on the eyeball coats and other ocular structures, as well as on the retrobulbar tissues.

Thus, the experimental studies performed have demonstrated that the proposed composition is capable of promoting the formation of a connective capsule and of increasing the elastic-strength characteristics of the sclera and renders no detrimental, toxic or irritative effect on the eyeball coats.

The proposed composition has been trialled clinically on 37 patients aged from 13 to 27. The proposed composition was injected under the Tenon's capsule onto the posteroexternal scleral surface. No complications were observed both during and after the injection. Late follow-up observation of the treatment results (up to 1.5 years) was made in 20 patients, the degree of myopia being from 5.0 to 12.0 D. In no case was progression of myopia observed. 12 patients exhibited a reduced degree of myopia by 1.0 to 2.0 D. Thermography indicated a temperature rise by 1.7° C. within early periods of time, which was concerned with increased hyperemia in the eyeball coats and was indicative of a more intensive nature of rofmation of a connective capsule on the scleral surface. This was confirmed by a reduced coefficient of strain of the sclera in 0.5 year after injection of the proposed composition and differed reliably from a change of said index in response to the injection of the known composition.

The proposed composition is to be extemporized by intermixing first dichlorodi-[2-methyl-3-hydroxy-4,5-di-di(hydroxymethyl)-pyridine] of copper (II) with an aqueous solution of ferrous oxide, cupric citrate, boric and hydrochloric acids, then the resultant solution is doped with a mixture of polyvinylpyrrolidone, acrylamide-hydrazide, and ethylacrylate. After thorough agitation of the resultant liquid gel, a 3-percent aqueous hydrogen peroxide is added thereto and the thus-obtained mixture is injected under the patient's Tenon's capsule onto the posteroexternal scleral surface.

As a result, the proposed composition envelops uniformly the posterior scleral surface and solidifies 2 or 3 minutes later to form an elastic foamed gel. Thus, a reinforcing cage is established on the scleral surface, aimed at preventing the sclera from being extended and hence at ensuring against further progression of myopia.

Afterwards (within the following 12 months) the proposed composition, while being gradually absorbed, contributes to formation of collagen and stimulates the growth of connective tissue on the scleral surface. As a result, the strength of the sclera is increased and the sclera in the posterior eye portion gets thicker and stronger.

To promote understanding, the following examples of the proposed composition are given below by way of illustration.

EXAMPLE 1

The proposed composition incorporates the following constituents (mass percent):

| | | |
|---|---|---|
| a mixture of polyvinylpyrrolidone, acrylamide-hydrazide, and ethylacrylate (1:1:1) | | 29.5 |
| an aqueous solution, containing the following ingredients (mg/l): | | 69.5 |
| hydrochloric acid | 940.0 | |
| boric acid | 4.12 | |
| ferrous oxide | 115.0 | |
| cupric citrate | 16.0 | |
| 3-percent aqueous hydrogen peroxide | | 0.89 |
| dichloridi-[2-methyl-3-hydroxy-4,5-di-(hydroxy-methyl)-pyridine] of copper (II) | | 0.11 |

Placed into a vial is 4.2 mg (0.11 mass percent) of dichlorodi-[2-methyl-3-hydroxy-4,5-(hydroxymethyl)-pyridine] of copper (II) in the form of a sterile powder, which is dissolved in 2.6 ml (69.5 mass percent) of an aqueous solution, containing hydrochloric acid (940 mg/l), boric acid (4.12 mg/l), ferrous oxide (115 mg/l), and cupric citrate (16 mg/l). Next a mixture of polyvinylpyrrolidone, acrylamide and ethylacrylate hydrazide (1:1:1), taken in amount of 1101.9 mg (29.5 mass percent) is dissolved in the thus-obtained suspension to produce a homogeneous liquid gel, which is subjected to thorough shaking and is then doped with an activator, i.e., a 3-percent aqueous hydrogen peroxide taken in an amount of 0.034 ml (0.89 mass percent). Then 1015 ml of the resultant mixture is injected under the Tenon's capsule onto the posteroexternal scleral surface, using the conventional technique. An analysis of the foamed hydrogel formed from the proposed composition has demonstrated it to appear as an elastic spongy conglomerate having a volume weight 0.46 g/cm³.

EXAMPLE 2

The proposed composition incorporates the following constituents (mass percent):

| | | |
|---|---|---|
| a mixture of polyvinylpyrrolidone, acrylamide-hydrazide, and ethylacrylate (1:1:1) | | 24.5 |
| an aqueous solution, containing the following ingredients (mg/l): | | 74.4 |
| hydrochloric acid | 940.0 | |
| boric acid | 4.12 | |
| ferrous oxide | 115.0 | |
| cupric citrate | 16.0 | |
| 3-percent aqueous hydrogen peroxide | | 0.84 |
| dichlorodi-[2-methyl-3-hydroxy-4,5-di-(hydroxy-methyl)-pyridine] of copper (II) | | 0.26 |

Placed into a vial is 8.1 mg (0.26 mass percent) of dischlorodi-[2-methyl-3-hydroxy-4,5-di-(hydroxymethyl)pyridine] of copper (II) in the form of a sterile powder, which is dissolved in 2.8 ml (74.4 mass percent) of an aqueous solution, containing hydrochloric acid (940 mg/l), boric acid (4.12 mg/l), ferrous oxide (115 mg/l), and cupric citrate (16 mg/l). The thus-obtained suspension dissolves 902.4 mg (24,5 mass percent) of a mixture of polyvinylpyrrolidone, acrylamide-hydrazide, and ethylacrylate (1:1:1). Then the resultant homogeneous liquid gel is subjected to thorough shaking, whereupon 0.032 ml (0.84 mass percent) of activator, viz., a 3-percent aqueous hydrogen peroxide is added thereto and 0.15 ml of the thus-obtained mixture is injected under the Tenon's capsule onto the posteroexternal scleral surface. An analysis of the foamed hydrogel formed from the proposed composition has demonstrated to appear as an elastic spongy conglomerate having a volume weight of 0.50 g/cm³.

EXAMPLE 3

The proposed composition incorporates the following constituents (mass percent):

| | | |
|---|---|---|
| a mixture of polyvinylpyrrolidone, acrylamide-hydrazide, and ethylacrylate (1:1:1) | | 18.8 |
| an aqueous solution, containing the following ingredients (mg/l): | | 80.1 |
| hydrochloric acid | 940.0 | |
| boric acid | 4.12 | |
| ferrous oxide | 115.0 | |
| cuprum citrate | 16.0 | |
| 3-percent aqueous hydrogen peroxide | | 0.79 |
| dichlorodi-[2-methyl-3-hydroxy-4,5-di-(hydroxymethyl)-pyridine] of copper (II) | | 0.31 |

Placed into a vial is 11.9 mg (0.31 mass percent) of dichlorodi-[2-methyl-3-hydroxy-4,5-di-(hydroxymethyl)-pyridine] of copper (II) in the form of a sterile powder, which is dissolved in 3.0 ml (80.1 mass percent) of an aqueous solution, containing hydrochloric acid (940 mg/l), boric acid (4.12 mg/l), ferrous oxide (115.0 mg/l), and cupric citrate (16 mg/l). The thus-obtained suspension dissolves 702.5 mg (18.8 mass percent) of a mixture of polyvinylpyrrolidone, acrylamide-hydrazide, and ethylacrylate (1:1:1). Then the resultant homogeneous liquid gel is shaken thoroughly, whereupon 0.03 ml (0.79 mass percent) of an activator, viz., a 3-percent aqueous hydrogen peroxide is added thereto, and 0.15 ml of the thus-obtained mixture is injected under the Tenon's capsule onto the posteroexternal scleral surface, using the conventional technique. An analysis of the foamed hydrogel thus formed from the proposed composition has demonstrated it to appear as an elastic spongy conglomerate having a volume weight of 0.57 g/cm³.

INDUSTRIAL APPLICABILITY

The proposed composition for treatment of progressive myopia finds application in opthalmological practice for treating progressive myopia in children and adults.

We claim:

1. A composition for treatment of progressive myopia, comprising a mixture of polyvinylpyrrolidone, acrylamide-hydrazide and ethylacrylate, an aqueous solution of an ferrous oxide, cupric citrate, boric and hydrochloric acids, and hydrogen peroxide, dichlorodi-[2-methyl-3-hydroxy-4,5-di-(hydroxymethyl)-pyridine] of copper (II) with the following mass-percent ratio of the starting components ingredients:

| | |
|---|---|
| a mixture of polyvinylpyrrolidone, acrylamide-hydrazide, and ethylacrylate (1:1:1) | 18.8 to 29.5 |
| an aqueous solution, containing the following ingredients, taken in mg/l: | 69.5 to 80.1 |
| hydrochloric acid | 940.0 |
| boric acid | 4.12 |
| ferrous oxide | 115.0 |
| cupric citrate | 16.0 |
| 3-percent aqueous hydrogen peroxide | 0.79 to 0.89 |
| dichlorodi-[2-methyl-3-hydroxy-4,5-di-(hydroxymethyl)-pyridine] of copper (II) | 0.11 to 0.31. |

* * * * *